US010646287B2

(12) United States Patent
Kogan

(10) Patent No.: US 10,646,287 B2
(45) Date of Patent: May 12, 2020

(54) SYSTEM WITH A MEDICAL INSTRUMENT AND A RECORDING MEANS

(71) Applicant: KUKA Deutschland GmbH, Augsburg (DE)

(72) Inventor: Yevgen Kogan, Augsburg (DE)

(73) Assignee: KUKA Deutschland GmbH, Augsburg (DE)

( * ) Notice: Subject to any disclaimer, the term of this patent is extended or adjusted under 35 U.S.C. 154(b) by 315 days.

(21) Appl. No.: 15/522,542

(22) PCT Filed: Oct. 29, 2015

(86) PCT No.: PCT/EP2015/002170
§ 371 (c)(1),
(2) Date: Aug. 28, 2017

(87) PCT Pub. No.: WO2016/074770
PCT Pub. Date: May 19, 2016

(65) Prior Publication Data
US 2017/0354469 A1     Dec. 14, 2017

(30) Foreign Application Priority Data
Nov. 13, 2014   (DE) .......................... 10 2014 016 843

(51) Int. Cl.
*A61B 34/30*       (2016.01)
*B25J 9/16*        (2006.01)
(Continued)

(52) U.S. Cl.
CPC ............. *A61B 34/30* (2016.02); *B25J 9/1682* (2013.01); *B25J 9/1689* (2013.01); *B25J 9/1692* (2013.01);
(Continued)

(58) Field of Classification Search
CPC ............ A61B 34/30; A61B 2034/2051; A61B 2034/2063; A61B 2034/2055;
(Continued)

(56) References Cited

U.S. PATENT DOCUMENTS 7,155,315 B2     12/2006 Niemeyer et al.
9,999,975 B2 *    6/2018 Frensch ................ B25J 9/1666
(Continued)

FOREIGN PATENT DOCUMENTS

DE     102010029275 A1    12/2011
DE     102013109677 A1     3/2015
(Continued)

OTHER PUBLICATIONS

European Patent Office; Search Report in International Patent Application No. PCT/EP2015/002170 dated Jan. 21, 2016; 6 pages.
(Continued)

*Primary Examiner* — David F Dunphy
(74) *Attorney, Agent, or Firm* — Dorton & Willis, LLP

(57) ABSTRACT

A method for automatically predetermining an intended movement of a manipulator arrangement of a medical system having a medical instrument and a recording means for generating images, wherein the recording means and/or the instrument is guided by the manipulator arrangement. The method includes establishing an intended transformation between a reference stationary in relation to the recording means and a reference stationary in relation to the instrument; monitoring a deviation between the intended transformation and a current transformation between the reference stationary in relation to the recording means and the reference stationary in relation to the instrument; and determining a reset movement of the manipulator arrangement
(Continued)

for returning the current transformation to the intended transformation when the deviation satisfies a predetermined condition.

20 Claims, 1 Drawing Sheet

(51) Int. Cl.
    *A61B 34/20*     (2016.01)
    *A61B 90/00*     (2016.01)

(52) U.S. Cl.
    CPC ........... *A61B 2034/2051* (2016.02); *A61B 2034/2055* (2016.02); *A61B 2034/2063* (2016.02); *A61B 2090/3612* (2016.02); *G05B 2219/39045* (2013.01); *G05B 2219/39046* (2013.01); *G05B 2219/39114* (2013.01); *G05B 2219/39397* (2013.01)

(58) Field of Classification Search
    CPC ........... A61B 2090/3612; B25J 9/1689; B25J 9/1682; B25J 9/1692; G05B 2219/39397; G05B 2219/39114; G05B 2219/39046; G05B 2219/39045
See application file for complete search history.

(56) References Cited

U.S. PATENT DOCUMENTS

| | | |
|---|---|---|
| 2013/0325030 A1 | 12/2013 | Hourtash et al. |
| 2013/0331644 A1 | 12/2013 | Pandya et al. |
| 2014/0051921 A1* | 2/2014 | Miller ............... A61B 1/00009 600/103 |
| 2014/0323803 A1 | 10/2014 | Hoffman et al. |

FOREIGN PATENT DOCUMENTS

| | | |
|---|---|---|
| WO | 2010078011 A1 | 7/2010 |
| WO | 2012078989 A1 | 6/2012 |

OTHER PUBLICATIONS

German Patent Office; Examination Report in German Patent Application No. 10 2014 016 843.3 dated Jul. 16, 2015; 10 pages.

* cited by examiner

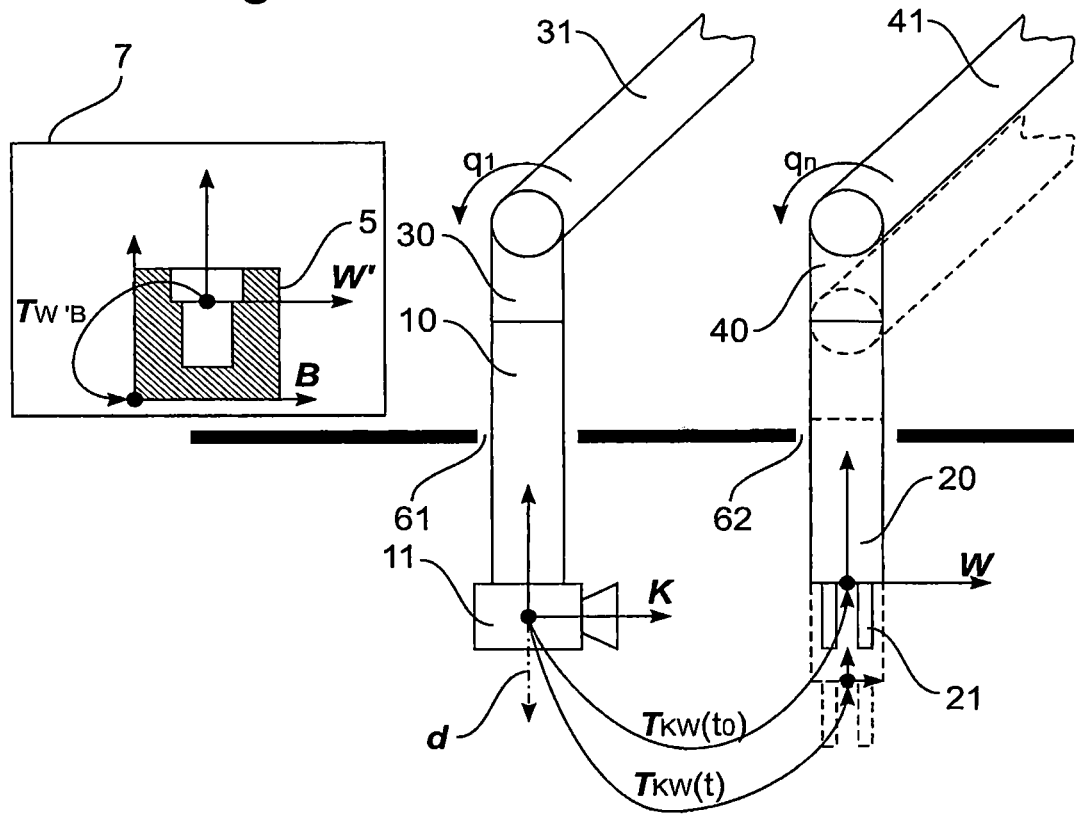
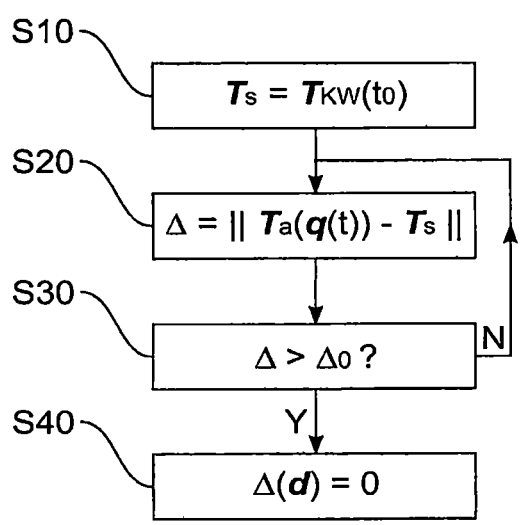

SYSTEM WITH A MEDICAL INSTRUMENT AND A RECORDING MEANS

CROSS-REFERENCE

This application is a national phase application under 35 U.S.C. § 371 of International Patent Application No. PCT/EP2015/002170, filed Oct. 29, 2015 (pending), which claims the benefit of German Patent Application No. DE 10 2014 016 843.3 filed Nov. 13, 2014, the disclosures of which are incorporated by reference herein in their entirety.

TECHNICAL FIELD

The present invention concerns a medical system, which comprises a manipulator arrangement, a medical instrument and a recording means for creating images, wherein the recording means and/or the instrument is guided by the manipulator arrangement, a method for automatically predetermining an intended movement of the manipulator arrangement as well as a computer program product for implementing such a method.

BACKGROUND

A system with an instrument robot, which guides a microinvasive medical instrument, and a camera-robot, which guides a microinvasive camera that generates images of an operational area of the instrument, is known from WO 2012/078989 A1.

WO 2012/078989 A1 proposes three methods for predetermining an intended movement of the camera robot. In a so-called stationary mode, the camera-robot invariably remains in one position. In a following mode, the intended movement of the camera robot is predetermined in such a way that the instrument or its tip is always positioned in the center of the visual field of the camera, i.e. of the generated image of the operational area. In a zoom mode, the camera is moved along a connecting axis in fixedly predetermined increments of 2 cm as soon as a viewing angle for capturing the tip of the instrument becomes too big or small.

SUMMARY

The object of the present invention is to improve the operation of a generic medical system. This object is achieved by a medical system and method as shown and described herein.

According to one aspect of the present invention, a medical system comprises a manipulator arrangement, a medical instrument, a recording means for creating images, and a control means, wherein the recording means and/or the instrument is guided by the manipulator arrangement.

In one embodiment, the manipulator arrangement comprises one or more manipulators, in particular robots. In one embodiment, each of these one or more manipulators comprise one or more, in particular by the control means actuatable, in particular actuated, rotary and/or linear joints, in particular at least six or more joints respectively. In one embodiment, one or more manipulators, in particular their bases, are stationary, and/or one or more manipulators, in particular their bases, are movable.

In one embodiment, the medical instrument is configured for minimally invasive use. In one embodiment, it comprises an instrument shaft, which can be inserted or is intended or configured to be inserted into a patient, in particular through an artificial or natural body orifice, and/or the inserted or for insertion configured area of which has a maximum circumference of at most 20 cm, in particular at most 5 cm. In one embodiment, the instrument comprises an end actuator, which can in particular be moved in an actuated manner relative to the instrument shaft, and is in particular intended for introducing and/or removing liquids and/or gases and/or for mechanical interaction, in particular cutting, clamping or the like. In one embodiment, the instrument, in particular its instrument shaft, is connected with at least one manipulator of the manipulator arrangement in a coupleable and in particular preferably detachable manner, and can thus be moved or guided by the manipulator arrangement.

In one embodiment, the recording means is configured for minimally invasive use. In one embodiment, it comprises a shaft which can be inserted or is intended or configured to be inserted into a patient, in particular through an artificial or natural body orifice and/or the inserted or for insertion configured area of which has a maximum circumference of at most 20 cm, in particular at most 5 cm. In one embodiment, the recording means comprises an end actuator, which can in particular be moved in an actuated manner or is stationary relative to the instrument shaft, and in particular intracorporeally or extracorporeally emits and/or receives ultrasound and/or, in particular visible or invisible, electromagnetic radiation or is intended or configured to do so. In one embodiment, the recording means, in particular its shaft, can be connected with at least one manipulator of the manipulator arrangement in a coupleable and in particular preferably detachable manner, and can thus be moved or guided by the manipulator arrangement. In one embodiment, the recording means further processes received ultrasound and/or received visible or invisible electromagnetic radiation, in particular in order to generate images, in particular of at least one part of the instrument, in particular its end actuator, and/or the surroundings thereof, or is intended or configured to do so. The recording means can in particular comprise a light source and/or an, in particular electronic, camera.

According to one aspect of the present invention, a method for automatic predetermination, in particular specifying or determining, an intended movement of the manipulator arrangement comprises the following steps which can in particular be implemented by the control means:

Determining an intended transformation between a recording means fixed reference and an instrument fixed reference;

Monitoring of a deviation between the intended transformation and a current transformation between the recording means fixed reference and the instrument fixed reference; and Determining a reset movement of the manipulator arrangement to return the current transformation to the intended transformation, if the deviation satisfies an in particular variable predetermined condition.

In one embodiment, the control means implements this predetermined intended or reset movement by appropriate actuation of joints of the manipulator arrangement or is configured to do this.

This allows the recording means to advantageously generate images of the instrument and its operational area: as long as the deviation between the intended transformation and the current transformation does not (yet) satisfy the predetermined condition, no reset movement of the manipulator arrangement is determined. Accordingly, in one embodiment, the recording means can then advantageously generate images with "fixed surroundings," which can in particular facilitate the control of the instrument by a surgeon on the basis of the pictures. On the other hand, if the predetermined condition is satisfied, a reset movement is determined, which returns the current transformation to the intended transformation, so that, after the reset movement is performed, the recording means can advantageously generate images, the perspective of which with respect to the instrument corresponds to a perspective before the reset movement, which can again in particular facilitate the control of the instrument by the surgeon on the basis of the images.

In contrast to this, in the following mode of WO 2012/078989 A1, the surroundings under a stationary instrument appear to "move" in the image, which makes control of the instrument by the surgeon on the basis of the images difficult. In the zoom mode of WO 2012/078989 A1, however, the camera is moved along the connecting axis in fixed specified increments, so that the perspective of the images changes in an unfavorable manner, which likewise makes control of the instrument by the surgeon on the basis of the images difficult.

In one embodiment, the recording means fixed reference is fixed (stationary) in relation to a component of the recording means, in particular its shaft or end actuator. In another embodiment, the recording means fixed reference is fixed (stationary) in relation to an image generated by the recording means, i.e. is fixed within such an image. For a more compact representation, they are both generally referred to here as the recording means fixed reference. The recording means fixed reference can in particular comprise, in particular be, a point or a one or multidimensional coordinate system.

In one embodiment, the instrument fixed reference is fixed (stationary) in relation to a component of the medical instrument, in particular its instrument shaft or end actuator. In another embodiment, the instrument fixed reference is fixed (stationary) in relation to an image of the instrument in an image generated by the recording means. For a more compact representation, they are both generally referred to here as the instrument fixed reference. The instrument fixed reference can in particular comprise, in particular be, a point or a one or multidimensional coordinate system.

In one embodiment, a transformation is an allocation between a recording means fixed reference and an instrument fixed reference, in particular an image or an image specification that displays, in particular transfers, the one reference on top of the other reference. If, in a simple embodiment, the references are fixed points x, y on instrument and recording means, or image, the connecting vector (x-y) can constitute this type of transformation. If the references in one embodiment are three-dimensional coordinate systems A, B, the image $T_{AB}$, which transforms vector $_Bx$ described in coordinate system B into vector $_Ax$ described in coordinate system A, can constitute this type of transformation. Such a transformation can, for example, be described or defined by the connecting vector of the origins of the two coordinate systems A, B and the rotation matrix $Rot_{AB}$ between the two coordinate systems, the Denavit-Hartenberg matrix or the like. In this regard reference is additionally also made to WO 2012/078989 A1, and its content is included in the present disclosure.

A transformation can therefore in particular describe, or be defined by, a relative position and/or orientation of a component of the recording means and a component of the medical instrument, i.e. component fixed references. Similarly, a transformation can in particular describe, or be defined by, a relative position and/or orientation of an image generated by the recording means and a depiction of the medical instrument in this image, i.e. image fixed references.

In one embodiment, the reset movement is predetermined on the basis of the deviation when the condition is satisfied, and/or independently of a relative movement between the instrument and the recording means that occurs after the condition is satisfied.

As a result of this, in one embodiment, a (further) relative movement between the instrument and the recording means, which occurs after the condition is satisfied, does not affect the reset movement predetermined on the basis of the deviation when the condition is satisfied. In other words, a recording area of the recording means can be returned to its original position and/or orientation relative to the instrument, even if the instrument and the recording means have since continued to move relative to one another. Additionally, or alternatively, such an advantageous reset movement, that is for example as visually undisturbing as possible, can be predetermined independent of any interim further relative movement between the instrument and the recording means. This can in particular facilitate control of the instrument by the surgeon on the basis of the images.

In one embodiment, the reset movement to return the current transformation to the intended transformation is determined on the basis of the deviation, in particular the deviation when the condition is satisfied, in particular such that this deviation decreases, preferably becomes minimal, in particular in such a way that the deviation decreases, at least for the most part, to zero. Accordingly, the deviation between the intended and the returned current transformation in one embodiment is, at least for the most part, equal to zero.

In one embodiment, the reset movement is predetermined with an in particular maximum or constant velocity, which is at least twice or at most one half of an in particular current, maximum, minimum, or average velocity of a relative movement between the instrument and the recording means. In a further development, the velocity of the reset movement is variably adjustable or predeterminable; an automatic and/or manual selection can in particular be provided between a first mode, in which the reset movement is predetermined with a velocity that is at least twice the velocity of the relative movement between the instrument and the recording means, and a second mode, in which the reset movement is predetermined with a velocity that is at most half the velocity of the relative movement between the instrument and the recording means.

Through the in particular selectable predetermination of a velocity, which is at least twice the maximum velocity of the relative movement between the instrument and the recording means, the reset movement can be performed very quickly, in particular abruptly, so that the generated images in one design are "fixed with respect to their surroundings" for long periods of time.

Through the in particular selectable predetermination of a velocity, which is at most half the velocity of the relative movement between the instrument and the recording means, the reset movement can be performed very slowly, in particular smoothly, so that, in the course of the reset movement, the generated images in one embodiment change only slowly with respect to their surroundings.

In one embodiment, the intended transformation is predetermined in particular variably on the basis of an identified, in particular current, transformation between the recording means fixed reference and the instrument fixed reference. The intended transformation can in particular be a current transformation that is identified at an in particular manually determined point in time. In this way, in one embodiment, the operator can set a desired perspective of the generated images, to which the reset movement returns. For this purpose, he can in particular position the instrument and the recording means relative to one another as desired, and predetermine a transformation identified in this position as the intended transformation.

In one embodiment, the intended transformation and the current transformation in particular selectively comprise a one, two or three-dimensional translation and/or an in particular one, two or three-dimensional rotation between the recording means fixed reference and the instrument fixed reference, in particular only one such translation or only one such rotation. By means of an appropriate selection, the reset movement in one embodiment can in particular advantageously comprise, in particular be, a one or multidimensional displacement and/or rotation, in particular about an optical axis of the recording means and/or perpendicular thereto. If, for example, the transformations comprise only a distance, in particular in the direction of the optical axis of the recording means or an image plane perpendicular thereto, a specific reset movement to return the current transformation to the intended transformation corresponds to a planar displacement without a change in orientation.

In one embodiment, the deviation comprises an in particular multidimensional difference between the intended and the current transformation, and/or an in particular one-dimensional mathematical norm, in particular a maximum norm or an amount norm, of this difference. Thus, in one embodiment, the deviation of the amount of a difference between the connecting vectors $(x(t_o)-y(t_o))$ and $(x(t)-y(t))$ (whereby $(x(t_o)-y(t_o))$ is the intended transformation and $(x(t)-y(t))$ is the current transformation), can describe or comprise, in particular be, the largest component of an in particular weighted difference of DENAVIT-HARTENBERG matrices, Euler or Cardan angles, quaternions or the like, which describe the intended or the current transformation. Accordingly, the predetermined condition can be satisfied when a distance and/or a rotation between the recording means fixed reference and the instrument fixed reference exceeds a predetermined value.

In one embodiment, a position and/or orientation of the recording means fixed reference and/or the instrument fixed reference and/or the intended transformation and/or the current transformation is determined on the basis of an identified pose of the manipulator arrangement, in particular of identified joint coordinates, in particular joint angles, of one or more manipulators of the manipulator arrangement.

From an identified pose of the manipulator arrangement guiding the instrument and/or the recording means, a position and/or orientation of the recording means and the instrument, and with it a recording means (component) fixed reference and/or an instrument (component) fixed reference, and/or a relative position and/or orientation of the recording means and the instrument to one another, and with it an intended and/or current transformation, can advantageously be determined in a manner known per se as so-called forward kinematics.

In one embodiment, a relative position and/or orientation of an image of the instrument in an image generated by the recording means can be determined from the relative position and/or orientation of the recording means and the instrument to one another that is determined on the basis of the identified pose of the manipulator arrangement. A relative position and/or orientation of the recording means fixed reference and the instrument fixed reference to one another, and with it an intended and/or current transformation, can then be determined. In a further development, the recording means is calibrated in advance, in particular to determine the parameters of the recording means.

Similarly, in another embodiment, such a relative position and/or orientation of a depiction of the instrument in an image generated by the recording means can also be determined by means of image recognition, with which the depiction is sought and identified within the image. A relative position and/or orientation of the recording means fixed reference and the instrument fixed reference to one another, and with it an intended and/or current transformation, can then be determined.

In one embodiment, the condition is satisfied, if a depiction of the instrument in the image generated by the recording means satisfies an in particular variable predetermined criterion, in particular a predetermined area of the depiction of the Instrument is outside a predetermined area of the image.

Additionally or alternatively, in one embodiment, the condition is satisfied if the deviation exceeds a predetermined one or multidimensional threshold value, i.e. in particular, if a relative position and/or orientation between the recording means and the instrument, which is described by a current transformation between the recording means fixed reference and the instrument fixed reference, changes (has changed) excessively in comparison to an initial position, which is described by the intended transformation. As explained above, in a further development, this threshold value can be predetermined such that the condition is met, if a depiction of the instrument in the image generated by the recording means satisfies an in particular variable predetermined criterion, in particular a predetermined area of the depiction of the instrument is outside a predetermined area of the image.

In one embodiment, the condition can be specified in a variable manner. In one embodiment this allows the operator to advantageously change the starting point of a reset movement predetermination.

In one embodiment, the reset movement of the manipulator arrangement to return the current transformation to the intended transformation is determined in such a way that a position and/or orientation of the instrument and/or a pose of the manipulator guiding the instrument by the reset movement, at least for the most part, does not change. The recording means thus follows the instrument, without interfering with the movement of the instrument initiated by the operator. In particular, in one embodiment, only one reset movement of one or more manipulators of the manipulator arrangement guiding the recording means is determined.

According to one aspect of the present invention, the control means of the medical system is configured for implementing a method described herein, or executes a method described herein. According to a further aspect of the present invention, a computer program product comprises a program code for implementing a method described herein, which is stored on a computer readable medium.

A means in the sense of the present invention, in particular the control means of the medical system, can be configured in terms of hardware and/or software, in particular an in particular digital processing unit, in particular a microprocessor unit, (CPU), which is preferably data- or signal-connected with a memory and/or bus system, and/or comprises one or more programs or program modules. The CPU can be configured to process commands, which are implemented as a program stored in a memory system, acquire input signals from a data bus and/or deliver output signals to a data bus. A memory system may comprise one or more, in particular different, memory media, in particular optical, magnetic, solid state and/or other non-volatile media. The program may be such that it embodies, i.e. is capable of executing, the methods described herein, so that the CPU can execute the steps of such methods and can thus in particular predetermine the intended movement.

BRIEF DESCRIPTION OF THE DRAWINGS

Further advantages and features of the invention will be apparent from the accompanying drawings and the description of the exemplary embodiments. For this purpose, partially in schematic form, the figures show:

FIG. 1: part of a medical system with a manipulator arrangement according to one embodiment of the present Invention; and FIG. 2: a method for automatically predetermining an intended movement of the manipulator arrangement according to one embodiment of the present Invention.

DETAILED DESCRIPTION

FIG. 1 shows a part of a medical system according to one embodiment of the present invention.

The medical system comprises a manipulator arrangement with two manipulators, of which only one end flange 30 or 40, and a part of an arm 31 and 41 connected to said end flange via a pivot joint with a rotation angle $q_1$ or $q_n$, is respectively indicated in FIG. 1.

The medical system further comprises a medical instrument designed for minimally invasive use with an instrument shaft 20, which is inserted into a patient through a body orifice 62, and an end actuator 21 for clamping or the like, which can be moved in an actuated manner relative to the instrument shaft. The instrument shaft 20 is connected to the end flange 40 in a detachable manner and can thus be moved or guided by means of the manipulator arrangement.

The medical system further comprises a recording means for generating images that is designed for minimally invasive use and has a shaft 10, which is inserted into a patient through a body orifice 61, and an end actuator 11 in the form of a micro camera, which is stationary in relation to the shaft and intracorporeally receives visible electromagnetic radiation that is further processed by the recording means to generate images 5 of the end actuator 21 and its operational surroundings. The shaft 10 is connected to the end flange 30 in a detachable manner and can thus be moved or guided by means of the manipulator arrangement.

The medical system further comprises a control means 7 in the form of a computer.

This control means implements a method according to one embodiment of the present invention, which will be explained in the following with reference to FIG. 2:

First, in Step S10, an intended transformation $T_s = T_{KW}(t_0)$ between a recording means fixed reference and an instrument fixed reference is determined.

As indicated in FIG. 1, the recording means fixed reference example may, for example be a coordinate system K, which is stationary relative to the camera 11. Similarly, the recording means fixed reference may, for example, also be a coordinate system B, which is stationary relative to the image 5 generated by the camera.

In an analogous manner, the instrument fixed reference may, for example, as indicated in FIG. 1, be a coordinate system W, which is stationary relative to the end actuator 21 or the instrument shaft 20. Similarly, the instrument fixed reference may, for example, also be a coordinate system W', which is stationary relative to the depiction of the instrument in the image 5 generated by the camera.

The transformation is suggested as an example in FIG. 1 by the image $T_{KW}$ between the coordinate systems K and W or the image $T_{W'B}$ between the coordinate systems W' and B. It describes the relative position and orientation of the camera 11 and the instrument shaft 20 or end actuator 21, or of the generated image 5 and the depiction of the instrument therein.

In each case the transformation $T_{KW}$ is determined by means of forward kinematics on the basis of the measured joint angle $q = (q_1, \ldots q_n)$ or an identified pose of the manipulator arrangement.

The transformation $T_{W'B}$ can likewise always be determined on the basis of the measured joint angle q while taking into account a field of view of the camera 11. Similarly, the transformation $T_{W'B}$, which conveys a relative position and/or orientation of the depiction of the end actuator 21 of the instrument in the image 5 generated by the recording means 11, can also be determined by means of image recognition.

The intended transformation is predetermined in Step S10 on the basis of a current transformation between the recording means fixed reference and the instrument fixed reference identified at time $t_0$. As an example, this is indicated by $T_s = T_{KW}(t_0)$ in the embodiment of FIG. 2.

A mathematical norm of a difference between the intended and a continuously identified current transformation $T_a(q(t))$, which is expressed as "$\|\ldots\|$" and determined from the joint angles $q = (q_1, \ldots q_n)$ of the manipulator arrangement, is then periodically or continuously determined in Step S20 as a deviation $\Delta$ between the intended transformation, and the respective current transformation between the recording means fixed reference and the instrument fixed reference. This is then monitored in Step S30, to see whether this deviation $\Delta$ exceeds a predetermined threshold value $\Delta_0$, i.e. to see whether, in particular, a relative position and/or orientation between the recording means and the instrument has changed excessively.

As soon as the deviation $\Delta$ exceeds the predetermined threshold value $\Delta_0$ (S30: "Y"), which is indicated as an example in FIG. 1 by a dotted line illustrating a deflected position of the medical instrument, a predetermined condition is satisfied, and in a Step S40 the control means 7 determines a reset movement d of the manipulator arrangement to return the current transformation to the intended transformation, which for illustration is indicated in FIG. 1 with a dash-dotted line.

In the exemplary embodiment, this condition is predetermined in such a way that it is satisfied if the depiction of the instrument in the image 5 generated by the recording means is outside a predetermined area of the image.

In Step S40, when the condition (S30 "Y") is satisfied, the reset movement d is determined on the basis of the deviation $\Delta$ in such a way that this deviation decreases, preferably to zero, ($\Delta(d) = 0$), for example by solving a minimization problem "d so that $\Delta(d) =$ minimum!" or something similar.

The control means can subsequently implement this predetermined intended or reset movement by means of appropriate actuation of the joints of the manipulator arrangement (not shown in FIG. 2).

In the embodiment, the reset movement can optionally be predetermined with a velocity dd/dt, which is at least twice or at most one half a velocity of a relative movement between the instrument and the recording means.

In Step S40, the reset movement of the manipulator arrangement to return the current transformation to the intended transformation is determined in such a way that a position and/or orientation of the end actuator 21 of the instrument does not change. The above-mentioned minimization problem is accordingly solved only by varying the joint angles of the manipulator 30, 31, which guides the camera 11.

Even though exemplary embodiments have been outlined in the foregoing description, it should be noted that a variety of modifications are possible. In addition, it should be noted that the exemplary embodiments are merely examples that are by no means intended to limit the scope of protection, the applications and the structure in any way. Rather, with the foregoing description, the skilled person is provided with a guide for implementation of at least one exemplary embodiment, whereby a variety of changes, in particular with respect to the function and arrangement of the described components may be made without departing from the scope of protection as it is emerges from the claims and the equivalent combinations of features.

While the present invention has been illustrated by a description of various embodiments, and while these embodiments have been described in considerable detail, it is not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit and scope of the general inventive concept.

LIST OF REFERENCE SIGNS

10 Shaft (recording means)
11 Camera (recording means)
20 Instrument shaft
21 End actuator
30, 40 End flange (manipulator)
31, 41 Arm (manipulator)
5 Image
61, 62 Body orifice
7 Control means
d Reset movement
B Recording means image fixed reference
K Recording means component fixed reference
$q_1, q_n,$
q Joint angle
T Transformation
W Instrument component fixed reference
W' Instrument image fixed reference
Δ Deviation

What is claimed is:

1. A method for automatically predetermining a desired movement of a manipulator arrangement of a medical system, the medical system comprising a medical instrument and a recording means for creating images, wherein at least one of the recording means or the instrument are guided by the manipulator arrangement, the method comprising:
   determining an intended transformation between a recording means-side reference and an instrument-side reference;
   monitoring a deviation between the intended transformation and a current transformation between the recording means-side reference and the instrument-side reference; and
   determining a reset movement of the manipulator arrangement to return the current transformation to the intended transformation when the deviation satisfies a predetermined condition;
   wherein the recording means-side reference is determined on the basis of an identified pose of the manipulator arrangement.

2. The method of claim 1, wherein the predetermined condition is based on a variable area of the medical instrument.

3. The method of claim 1, wherein the reset movement is predetermined independently of a relative movement between the instrument and the recording means after the condition is satisfied.

4. The method of claim 3, wherein the reset movement is predetermined on the basis of the deviation when the condition is satisfied.

5. The method of claim 1, wherein the reset movement is predetermined with a velocity that is at least twice, or at most half, of a velocity of a relative movement between the instrument and the recording means.

6. The method of claim 5, wherein the velocity with which the reset movement is predetermined is at least one of a maximum velocity or a constant velocity.

7. The method of claim 1, wherein the intended transformation is predetermined based on an identified transformation between the recording means-side reference and the instrument-side reference.

8. The method of claim 7, wherein the intended transformation is variably predetermined.

9. The method of claim 1, wherein the intended transformation and the current transformation comprise at least one of a translation or a rotation between the recording means-side reference and the instrument-side reference.

10. The method of claim 9, wherein at least one of:
   the translation is a one-, two-, or three-dimensional translation; or
   the rotation is a one-, two-, or three-dimensional rotation.

11. The method of claim 1, wherein the deviation comprises at least one of a mathematical norm or a difference.

12. The method of claim 11, wherein at least one of:
   the norm is a one-dimensional norm; or the difference is a multi-dimensional difference.

13. The method of claim 1, wherein the condition is satisfied when an image of the instrument generated by the recording means satisfies a predetermined criterion.

14. The method of claim 13, wherein the predetermined criterion is variable.

15. The method of claim 1, wherein:
   the recording means is configured for at least one of:
      a) intracorporeal transmission,
      b) intracorporeal reception,
      c) extracorporeal transmission, or
      d) extracorporeal reception; and
   the at least one transmission or reception comprises at least one of:
      i) transmission or reception of visible electromagnetic radiation,
      ii) transmission or reception of invisible electromagnetic radiation, or
      iii) transmission or reception of ultrasound.

16. The method of claim 1, wherein at least one of the recording means or the instrument is at least one of:
   configured for minimally invasive use; or
   comprises a shaft that is movable by the manipulator arrangement to be inserted through a body orifice, and an end actuator.

17. The method of claim 1, wherein the intended transformation is determined based on an identified pose of the manipulator arrangement.

18. The method of claim 1, wherein the recording means-side reference is located on a shaft or an end actuator of the recording means.

19. A medical system, comprising:
a manipulator arrangement;
a medical instrument;
a recording means for creating images; and
a controller;
wherein at least one of the recording means or the instrument is guided by the manipulator arrangement; and
wherein the controller includes program code stored in a non-transitory, computer-readable storage medium, and the program code, when executed by the controller, implements the method of claim 1.

20. A computer program product including program code stored on a non-transitory, computer readable medium, wherein the program code, when executed by a computer implements the method of claim 1.

* * * * *